(12) United States Patent
Roger

(10) Patent No.: US 8,942,788 B2
(45) Date of Patent: Jan. 27, 2015

(54) IMAGE GUIDED SURGERY

(75) Inventor: Gregory James Roger, Sydney (AU)

(73) Assignee: Advanced Surgical Design & Manufature Limited, St. Leonards (AU)

( * ) Notice: Subject to any disclaimer, the term of this patent is extended or adjusted under 35 U.S.C. 154(b) by 1579 days.

(21) Appl. No.: 11/991,826

(22) PCT Filed: Sep. 8, 2006

(86) PCT No.: PCT/AU2006/001327
§ 371 (c)(1),
(2), (4) Date: Apr. 27, 2009

(87) PCT Pub. No.: WO2007/030866
PCT Pub. Date: Mar. 22, 2007

(65) Prior Publication Data
US 2009/0216116 A1    Aug. 27, 2009

(30) Foreign Application Priority Data
Sep. 12, 2005    (AU) ................................ 2005905017

(51) Int. Cl.
*A61B 5/05*         (2006.01)
*A61B 17/15*        (2006.01)
*A61B 19/00*        (2006.01)

(52) U.S. Cl.
CPC ............... *A61B 17/155* (2013.01); *A61B 19/54* (2013.01); *A61B 19/5244* (2013.01); *A61B 2019/5251* (2013.01); *A61B 2019/5255* (2013.01); *A61B 2019/5263* (2013.01); *A61B 2019/5416* (2013.01); *A61B 2019/5425* (2013.01); *A61B 2019/5437* (2013.01); *A61B 2019/547* (2013.01); *A61B 2019/5483* (2013.01)

USPC ......................................................... 600/426

(58) Field of Classification Search
CPC .............................. A61B 17/155; A61B 19/54
USPC ......................................................... 600/426
See application file for complete search history.

(56) References Cited

U.S. PATENT DOCUMENTS

| | | | |
|---|---|---|---|
| 4,952,213 A * | 8/1990 | Bowman et al. | 606/79 |
| 5,249,581 A | 10/1993 | Horbal et al. | |
| 5,649,928 A * | 7/1997 | Grundei | 606/88 |
| 6,205,411 B1 | 3/2001 | DiGioia, III et al. | |
| 6,385,475 B1 | 5/2002 | Cinquin et al. | |
| 6,533,737 B1 | 3/2003 | Brosseau et al. | |
| 2001/0034530 A1* | 10/2001 | Malackowski et al. | 606/130 |
| 2004/0122436 A1* | 6/2004 | Grimm | 606/87 |
| 2004/0172044 A1* | 9/2004 | Grimm et al. | 606/130 |
| 2004/0254584 A1 | 12/2004 | Sarin et al. | |
| 2005/0137599 A1 | 6/2005 | Masini | |

FOREIGN PATENT DOCUMENTS

WO    WO 02/067783 A2    9/2002
WO    WO 2005/023128 A1    3/2005

* cited by examiner

*Primary Examiner* — Long V. Le
*Assistant Examiner* — Bo J Peng
(74) *Attorney, Agent, or Firm* — Wolf, Greenfield & Sacks, P.C.

(57) ABSTRACT

A bone marker device for use in surgery. The device has attachment means which is/are attachable to bone that will ultimately be resected during the surgery. A guiding device that is removably securable to the bone of a patient adjacent to the joint and on which the bone marker device may be mounted. A guide member of the guiding device has a slot for receiving a bone resector and enabling accurate resection of bone around the joint.

21 Claims, 9 Drawing Sheets

IMAGE GUIDED SURGERY

CROSS-REFERENCE TO RELATED APPLICATIONS

The present application claims priority from Australian Provisional Patent Application No 2005905017 filed on 12 Sep. 2005, the content of which is incorporated herein by reference.

FIELD OF THE INVENTION

The present invention relates to devices and methods for use in the field of image guided surgery, particularly in the field of arthroplasty.

BACKGROUND OF THE INVENTION

The human knee is an example of a joint that is capable of complex motion including flexion/extension, adduction/abduction, anterior femoral-tibial shift, and axial rotation. Due to the inability of damaged cartilage to repair itself after injury, the typical treatment for patients with degeneration of the knee is the undertaking of a total knee replacement with a patello-femoral-tibial prosthesis.

Successful knee replacement with a prosthesis requires that the bearing surfaces allow, as much as possible, the knee to have a natural range of movement as determined by the ligaments and soft tissue surrounding the knee. This movement includes flexion/extension, roll back of femur on the tibia and finally rotation of the femur on the tibia at all angles of flexion.

One solution to date has been the "meniscal knee" developed by Goodfellow and O'Connor in Oxford, England (see U.S. Pat. No. 4,085,466). This knee provides a three part articulation comprising a curved femoral surface, a flat tibial surface and a meniscal bearing between the femoral and tibial surfaces. The meniscal bearing is normally formed of a suitable synthetic plastics material such as ultra high molecular weight polyethylene. It has a flat lower surface that slides on the tibial surface and a concave upper surface that receives the femoral surface. Constraint, and the shear stresses that go with it, is generally avoided as the meniscal bearing slides about on the flat tibial surface as the knee flexes, rolls and rotates.

While development of the meniscal knee has been well received there are a number of difficulties still inherent in the placement of prostheses of this and other types. The surgical placement of such prostheses has to be very precise and technical failure for this reason is common.

Accurate bone cuts are important for successful knee or other joint replacement surgery. The accuracy is assessed in terms of the flatness of the cut (which is a function of the stability of the saw guide and the accuracy of the saw system), the orientation of that cut within the body, and the accuracy of the cut with reference to other cuts. These latter two are most susceptible to improvement through use of guided and navigated orthopaedic surgery.

Navigation and robot systems are becoming an increasingly appropriate technology for use in knee and other joint replacement. For example, several systems exist for navigation of the knee to aid alignment of the standard total knee bone cuts. In use of such systems, in some cases the first step is for the patient to be scanned pre-operatively using computer aided tomography (or CT) techniques. In this way, the three dimensional "form" of the patient's bones is stored in a computer's memory. In addition, three dimensional data for the knee implant to be used by the surgeon, or for a range of possible knee implants which could be used by the surgeon, may also be stored in the computer's memory.

During the knee replacement operation an image of the bones is displayed on a computer screen so that the surgeon and others involved in the joint replacement are provided with the necessary information to perform the surgery. Alternatively a process to register the patient's actual bones from particular landmarks may be undertaken. This is typically performed after sensors or markers are fixed to the bones to coordinate the screen image and data capture with the position of the patient's bones. Bone cuts can then be made to suit the implant after sizing and judging the positions of the components on the computer screen. In addition, kinematic information may be gathered once the bones are "registered" allowing range of motion and leg alignment to be documented.

This technique can assist in ensuring that each of the components of the implant has controlled orientation relative to the bone onto which it will be implanted. This "landmark" technique replicates most existing systems for knee replacement that do not involve such a computer.

The use of sensors or markers attached to the bones in navigated surgery can be a problem due to the fact that the required holes to affix the pins securely holding the sensors are a potential stress riser and a track for infection.

Cutting guides are also typically employed to ensure that the bone saw used to resect bony tissue performs resections corresponding to mating surfaces of the prosthetic component. For example, in a femoral knee replacement, cutting guides or blocks are temporarily secured to the distal end of the femoral shaft, and include slots into which the blade of an oscillating saw is inserted to shape the end of the bone in accordance with corresponding surfaces of the prosthetic element. These cutting guides are also affixed to the bone temporarily, yet securely, with pins or screws.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is a bone marker device for use in conjunction with a bone mapping system, the bone marker device having a bone attachment means that is attachable to cancellous bone or bone that is to be resected following its mapping.

According to a second aspect, the present invention is a bone marker device for use in conjunction with a bone mapping system, the bone marker device having a bone attachment means that is attachable to a location in bone that is close enough to the resection lines to allow fixation without extension of the incision or invasion of cortical bone by the attachment means.

In one embodiment, the bone marker device can have one, two or more than two markers. The markers can be reflectors that reflect visible or non-visible light. For example, the markers can be infra-red markers. In another embodiment, the markers can be used as part of an ultrasonic system and comprise an ultrasonic or electro-magnetic emitter or receiver. In yet another embodiment, the bone marker device can have all the same type of marker or two or more different types of markers.

In yet another embodiment, the markers can be mounted to a post. The post can comprise the bone attachment means or be connectable thereto.

In another embodiment, the post can be adjustably or non-adjustably connectable to an attachment means in the form of a bone pin or bone screw. In one embodiment, the pin or screw can be self-tapping or be positionable in a suitable hole formed in the bone. In yet another embodiment, the bone in which the pin or screw is inserted is resected following the bone mapping undertaken by the bone mapping system.

The bone pin or bone screw may include a plate member extending outwardly from a portion of the pin or screw, said plate member having a face that is engageable with an outer surface of the bone to which the pin or bone screw is attached.

The bone screw may comprise an elongate body extending from a first end to a second end wherein the entire length of the bone screw is threaded. The threaded length secures the bone screw in the lesser amount of bone typically available if the bone is to be part of the resection during surgery.

In a third aspect, the present invention provides a bone marker device for use in conjunction with a bone mapping system, the bone marker device including:

at least one marker connectable to;

a bone attachment member, said bone attachment member comprising a bone screw extending from a first end to a second end, said bone screw having a screw thread along its entire length and a plate member that extends radially outwardly from a region of the bone screw at or adjacent to the first end, said plate member having a face that is engageable with an outer surface of a bone to which the bone screw is attachable;

wherein the bone attachment member is attachable to cancellous bone or bone that is to be resected during an operative procedure.

According to a fourth aspect, the present invention is an apparatus for use in joint replacement surgery, the apparatus comprising:

a guide member that is removably securable to a bone at or adjacent the joint, the guide member having at least one slot for receiving a bone resector; and at least one bone marker device mounted to the guide member for use in conjunction with a bone mapping system.

In this aspect, the bone marker device can have one or more of the features of the bone marker device according to the first or second aspects of the invention. In one embodiment, the bone marker device can be adjustably mounted to the guide member. In another embodiment, the bone marker device can be non-adjustably mounted to the guide member.

The apparatus can be securable to bone that is to be resected in the normal course of the joint replacement surgery. In another embodiment, the apparatus can be securable to cancellous bone at or near the joint.

Mounting of the guide member to the bone can be achieved through use of a pin or bone screw that is secured to the bone. The pin or bone screw preferably extends through the bone at or near the joint. In one embodiment, the pin or screw can extend through bone that is to be resected as part of the joint surgery. The pin or bone screw may also have a plate member which extends radially outwardly from a portion of the pin or bone screw and which stabilises the pin or bone screw in cancellous bone, using a combination of compression through thread form and a broader plate to create stability. The bone screw itself may also be threaded along its entire length, securing the bone screw in the lesser amount of bone typically available if the bone is to be part of the resection during surgery.

In yet a further embodiment, the guide member can have its position adjusted relative to the pin or bone screw. For example, the guide member can be pivotally mounted to the pin or bone screw to allow appropriate pivotal movement of the guide member relative to the pin or bone screw.

In yet another embodiment, the guide member can comprise extender members that are pivotally mounted to the pin or bone screw on opposed sides of the bone. These extender members can extend from the pin or screw to the main body member. In another embodiment, the extender members can extend to respective secondary members. The secondary members can extend at a right angle to the extender members or at some other angle. In a preferred embodiment, the secondary members can be adjustably mountable to the extender members. The respective secondary members can be independently adjustable if required.

In a still further embodiment, the guide member can comprise a body member. The body member preferably can have said at least one slot for the bone resector. The body member can be mounted to and extend between the secondary members. In one embodiment, the body member can be adjustably mountable to the secondary members. In another embodiment, the body member can be non-adjustably mounted to the secondary members.

The potential pivotal adjustment of the extender members together with the adjustable mounting of the secondary members on the extender members provides an apparatus that can be adjusted as necessary to ensure said at least one slot is positionable in the required position to ensure accurate bone resection. The guide member can comprise one or more reference pins or members.

The bone resection can be performed using an oscillating bone saw.

In a still further embodiment, the apparatus can be removed from the pin or screw mounted in the bone and replaced with a secondary apparatus that is adapted to be used in the resection of a different portion of bone. For example, and in the case of the distal femur, the first apparatus can be adapted to be used in the resection of the anterior femur. It can then be removed and a secondary apparatus can be mounted to the pin or screw that is adapted to be used in the resection of the distal femur. Once these relatively more critical resections have been made, the apparatus can be removed and the remaining cuts can be made using normal cutting guides.

According to a still further aspect, the present invention is a method of resecting bone in joint replacement surgery comprising:

removably securing the apparatus as defined herein to a bone location;
mapping the bone;
if required, adjusting the apparatus; and
resecting the bone.

BRIEF DESCRIPTION OF THE DRAWINGS

By way of example only, preferred embodiments of the invention are now described with reference to the accompanying drawings, in which.

PREFERRED MODE OF CARRYING OUT THE INVENTION

While the following description is directed to knee replacement surgery it will be appreciated that the present invention has a broader application to other orthopaedic procedures including replacement of other joints of a patient.

In a typical knee replacement surgery, the patient is set up on the operating table in a supine position after preoperative cleaning of the leg. A thigh tourniquet is generally used to aid surgical exposure. The knee joint is usually approached anteriorly through a medial parapatellar approach although a lateral or subvastus approach is used by some surgeons. Osteophytes and intra-articular soft-tissues are then cleared.

Bone cuts or resections are then made in the distal femur 11 to remove sufficient and appropriate portions of bone to allow attachment thereto of the femoral component. The various resections are made in a predetermined manner in correspondence with the inner surfaces of the implant.

Figure 1:
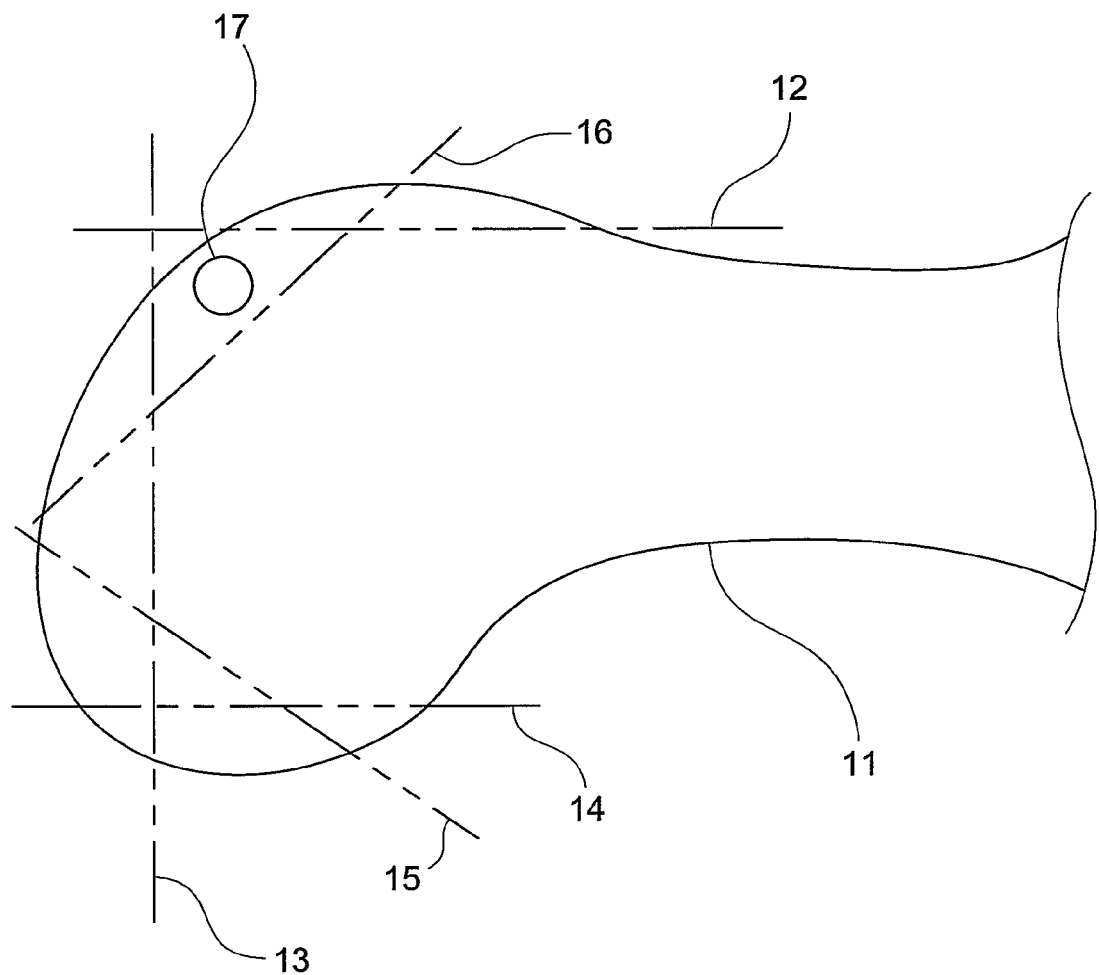
FIG. 1 is a view of the distal femur indicating the location of desired resections to allow placement of the femoral component of a prosthesis.

FIG. 1 provides an indication of where bone resection typically needs to be made. To ensure appropriate positioning and alignment of the femoral component of the prosthesis it is critical to appropriately position the saw guide such that the anterior chamfer cut 12 and distal femoral articular surface cut 13 are made in the appropriate location and at the appropriate angle. The appropriate location for the posterior chamfer cut 14, the posterior-articular surface cut 15, and the anterior articular surface cut 16 can be more readily achieved once the initial two bone resections have been performed.

FIG. 1 also depicts one suitable possible location 17 for a bone pin that is used in conjunction with other devices (as described below) in the performance of the knee replacement surgery.

Figure 2:
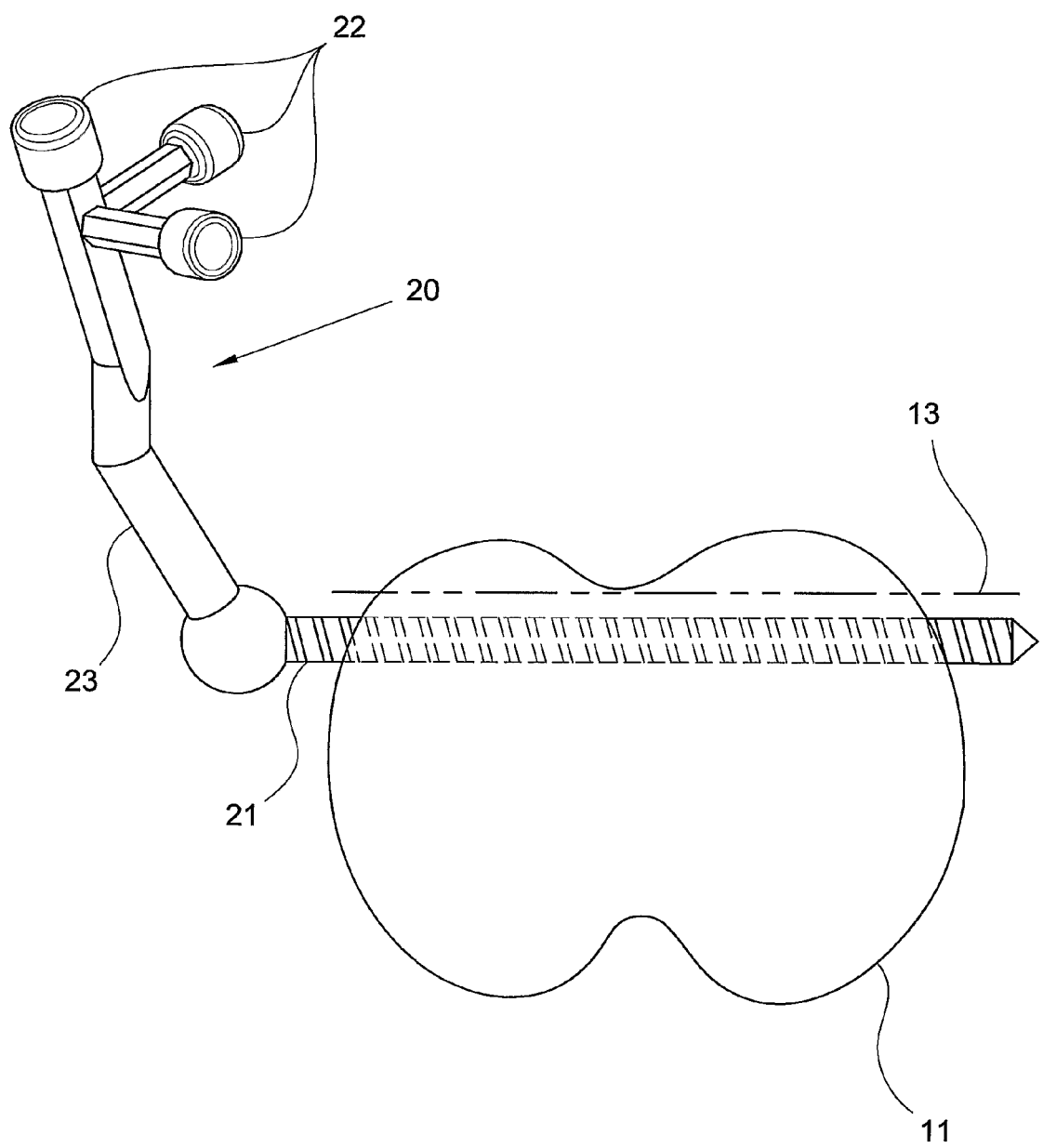
FIG. 2 is an end view of the distal femur with a bone marker device mounted thereto.
Figure 3:
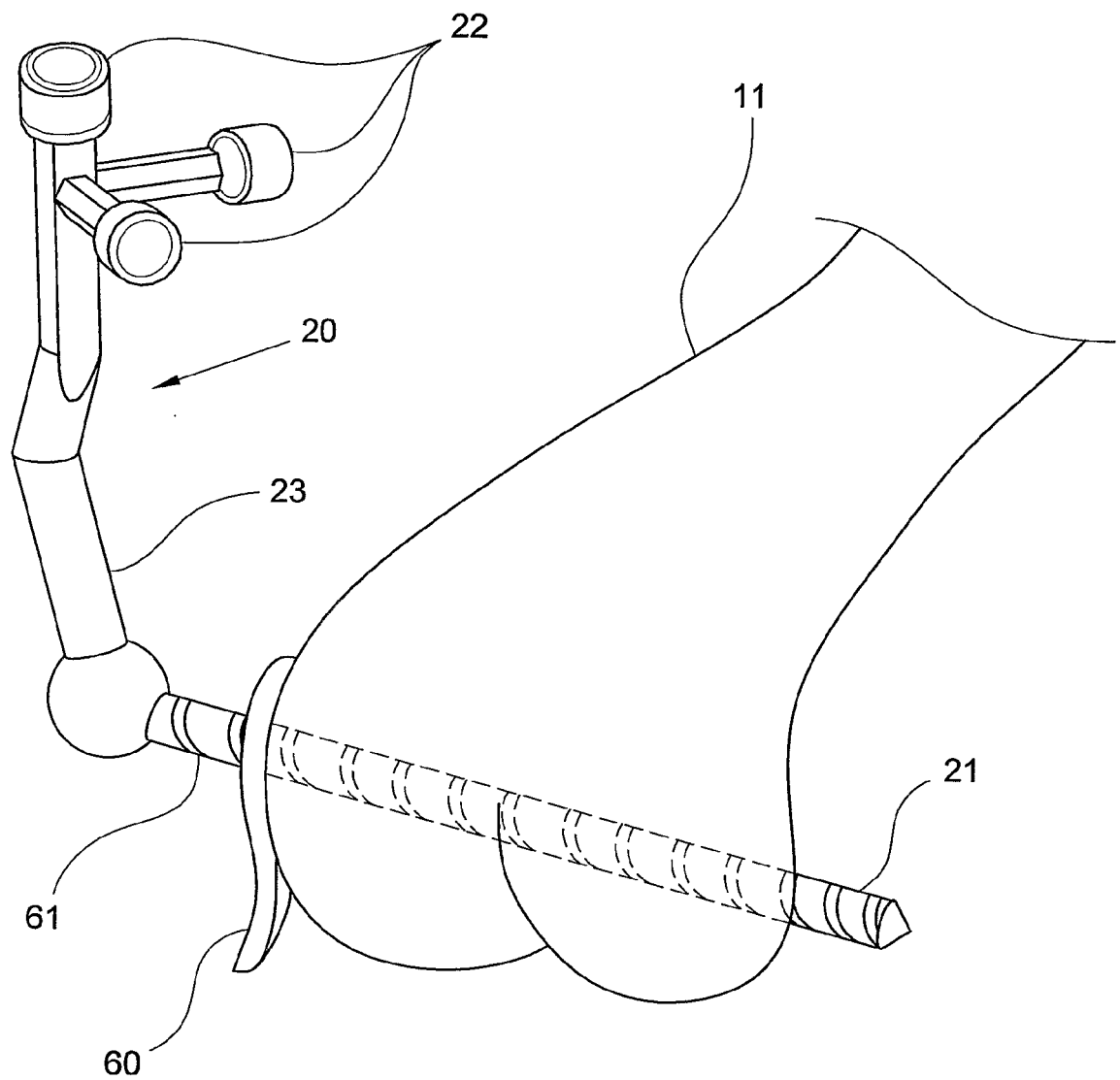
FIG. 3 is a further simplified view of the distal femur of FIG. 2.

One embodiment of a bone marker device according to the present invention is depicted generally as 20 in FIGS. 2 and 3. The bone marker device is adapted to be used in conjunction with a computerised bone mapping system that is used by the surgeon during the knee replacement surgery. The attached Figures are simplified and only depict those portions of the knee necessary to understand the function of the marker device 20.

The depicted bone marker device 20 comprises a pin 21 that is mountable to the bone at the location 17 depicted in FIG. 1. It is to be noted that location 17 is in a location that is ultimately resected. The use of this location for the mounting of the bone marker device 20 has the advantage of not having to make an unnecessarily larger incision or a puncture incision in which to place the device 20. Also, any damage caused to the femur 11 by placement of the marker 20 is done in a location that is ultimately removed in any event. The pin 21 of the bone marker device 20 is also, however, attachable to cancellous bone or bone that is not to be resected following its mapping.

In the depicted embodiment, the bone marker device 20 has a number of reflectors 22 mounted on a post 23 that extends from the pin 21. The depicted reflectors 22 reflect visible light, however, alternative marker types can be envisaged. For example, the markers can be infra-red markers or part of an ultrasonic system and comprise an ultrasonic emitter or receiver.

The pin 21 is adapted to secure the markers to the bone. Because there is a lesser amount of bone typically available if the bone is to be part of the resection during surgery, the pin includes a plate member 60 adjacent a first end 61 of the pin 21. The plate member 60 stabilises the pin 21 in the lesser amount of bone.

Figure 4:
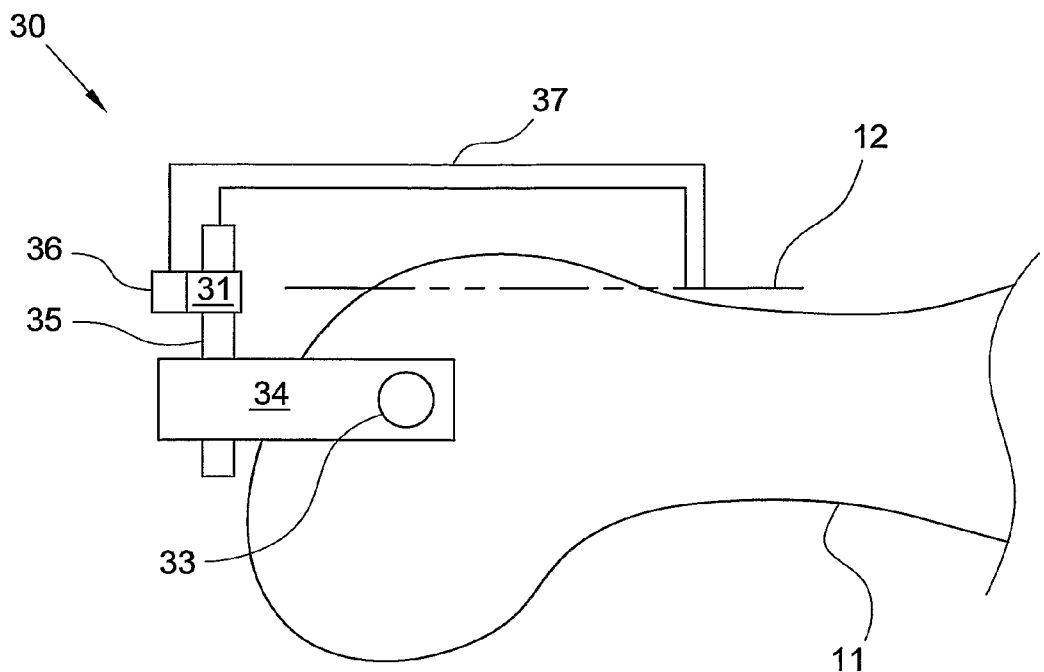
FIGS. 4, 5 and 6 are further views of the distal femur with an apparatus for use in guiding initial bone resections mounted thereto.
Figure 5:
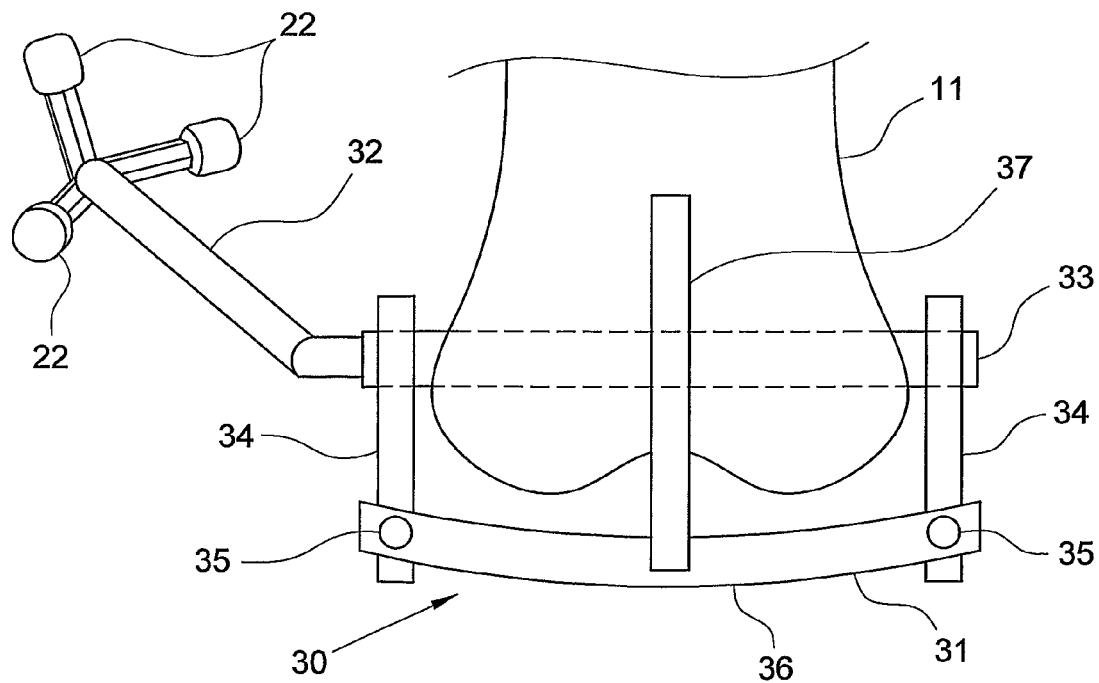
Figure 6:
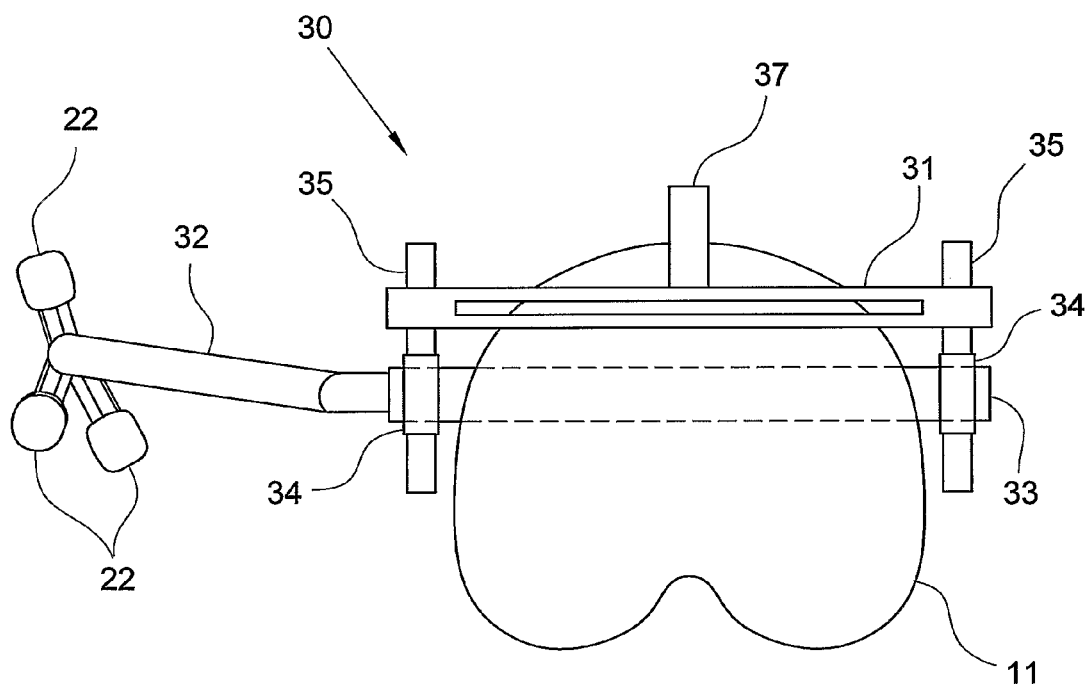

An apparatus for use in appropriately guiding the bone saw in forming the anterior chamfer cut 12 in the distal femur 11 is depicted generally as 30 in FIGS. 4-6. The apparatus 30 has both a guide member 31 having a slot for receiving a bone resector and a bone marker device 32 that is mounted to the guide member for use in conjunction with a bone mapping system.

The bone marker device 32 of this embodiment can have one or more of the features of the bone marker device 20 described above. In this embodiment, the bone marker device 32 is adjustably mounted to the guide member 30.

In the depicted embodiment, the apparatus 30 is securable to a location on the bone that is to be resected in the joint replacement surgery. Again, it will be appreciated that the apparatus could be securable to cancellous bone at or near the joint.

Mounting of the guide member to the bone 11 is achieved through use of a pin 33 that is secured to the bone 11. The pin 33 extends through the bone 11 at or near the joint.

The guide member is pivotally mounted to the pin 33 to allow appropriate pivotal movement of the guide member relative to the pin 33. Extender members 34 are pivotally mounted to the pin 33 on opposed sides of the bone 11. These extender members 34 extend from the pin 33 to respective secondary members 35. The secondary members 35 extend at a right angle to the extender members 34. The secondary members 35 are adjustably mountable to the extender members 34 so that the height of the guide member 31 is adjustable. As depicted in FIG. 6, the respective secondary members 35 are independently adjustable if required.

The guide member 31 comprises a body member 36 that has the slot for the bone resector. The body member 36 is mounted to and extends between the secondary members 35.

The potential pivotal adjustment of the extender members 34 together with the adjustable mounting of the secondary members 35 on the extender members 34 provides an apparatus that can be adjusted as necessary to ensure the slot of the guide member 31 is positionable in the required position to ensure accurate bone resection. As depicted, the apparatus 30 can also comprise a reference member 37.

While not depicted, the bone resection can be performed using a bone saw or other suitable device.

Figure 7:
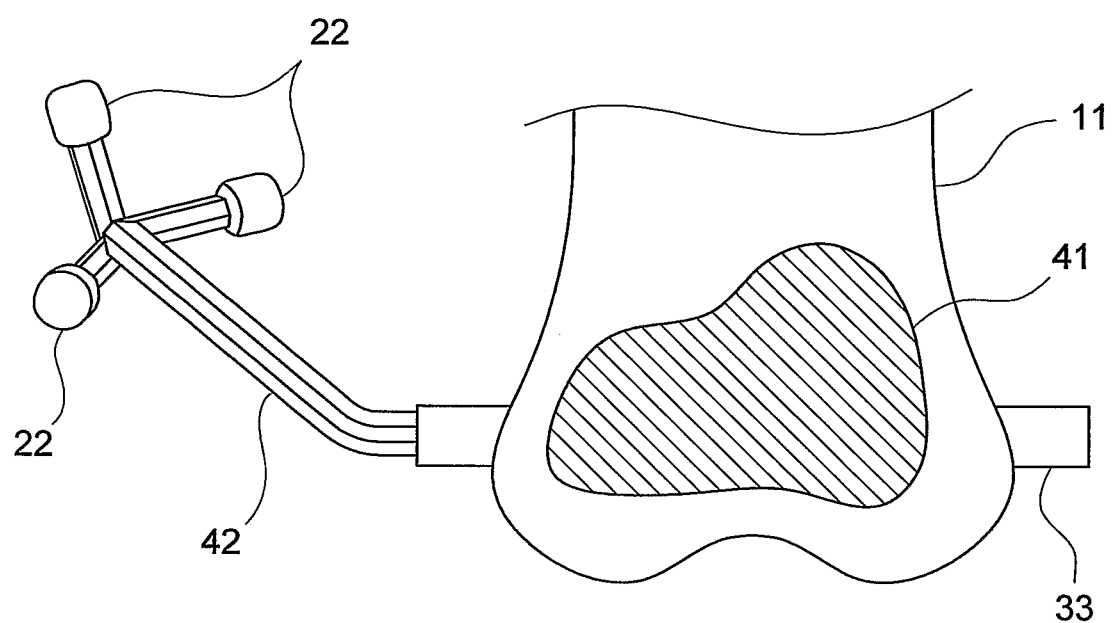
FIGS. 7, 8 and 9 are still further views of the distal femur with another apparatus for use in guiding bone resections mounted thereto.
Figure 8:
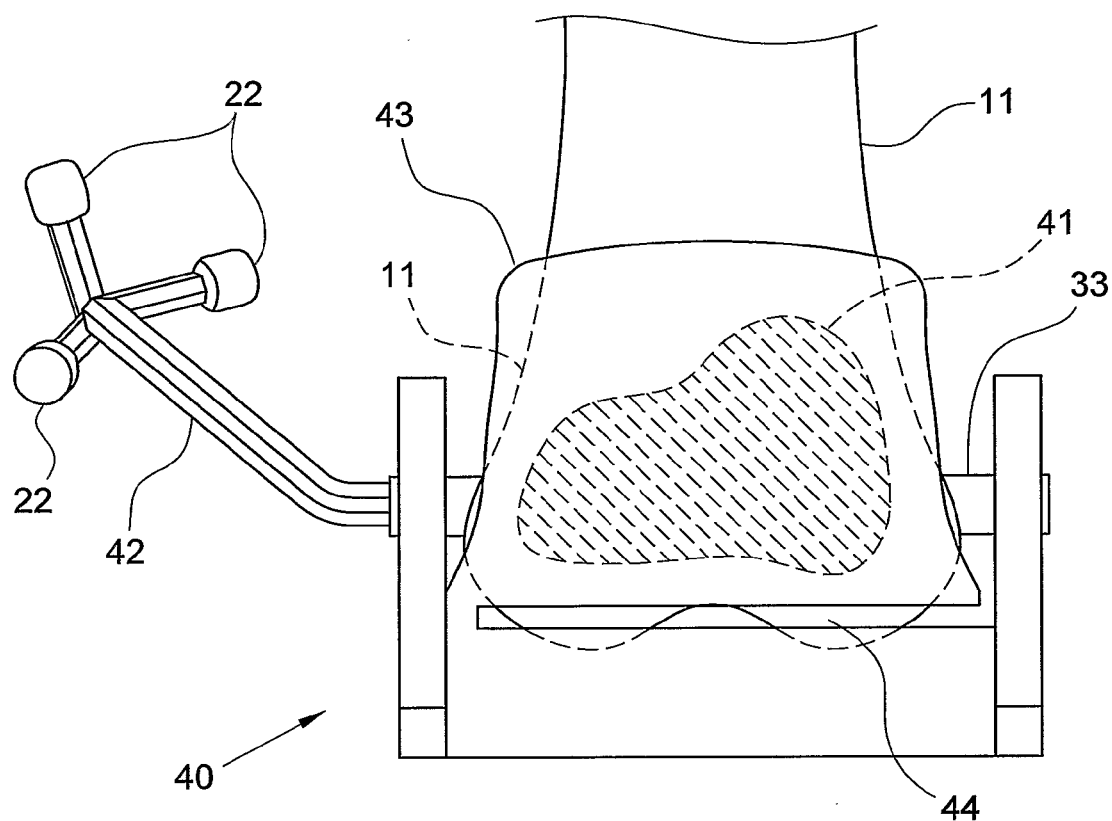
Figure 9:
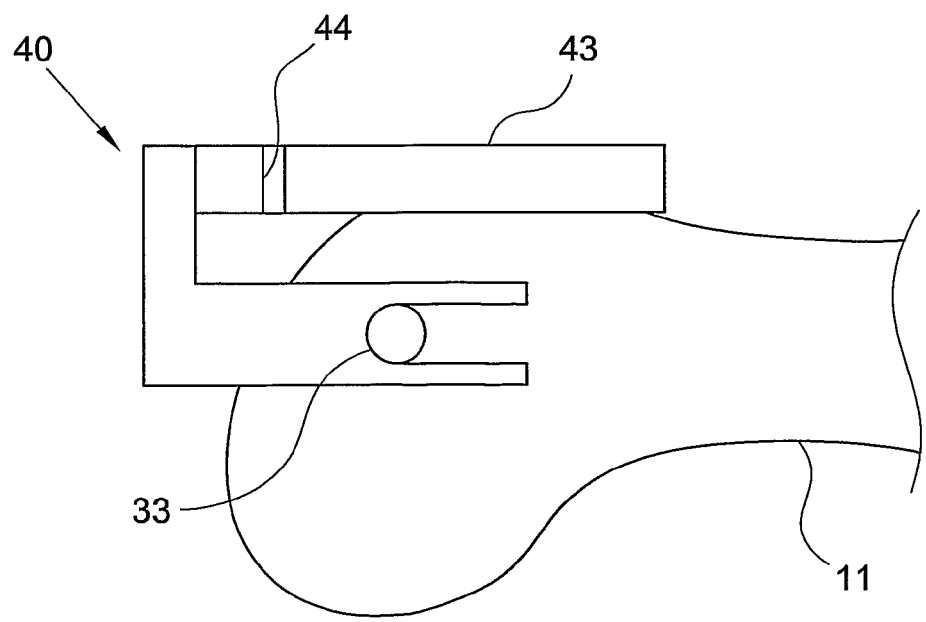

As depicted by FIGS. 7-9, the apparatus 30 can be removed from the pin 33 mounted in the bone 11 and replaced with a secondary apparatus that is adapted to be used in the resection of a different portion of bone. For example, and in the case of the distal femur 11, the first apparatus 30 can be adapted to be used in the resection of the anterior femur. It can then be removed and a secondary apparatus, generally depicted as 40 in FIGS. 7-9, can be mounted to the pin 33 and be adapted to be used in the resection of the distal femur. Once these relatively more critical resections have been made, the apparatus can be removed and the remaining cuts can be made using normal cutting guides.

FIG. 7 depicts the location of the previously made anterior resection 41. As depicted, the apparatus 40 can be mounted to the pin 33. The apparatus 40 again has reflectors 22 mounted to a post 42.

Figure 10:
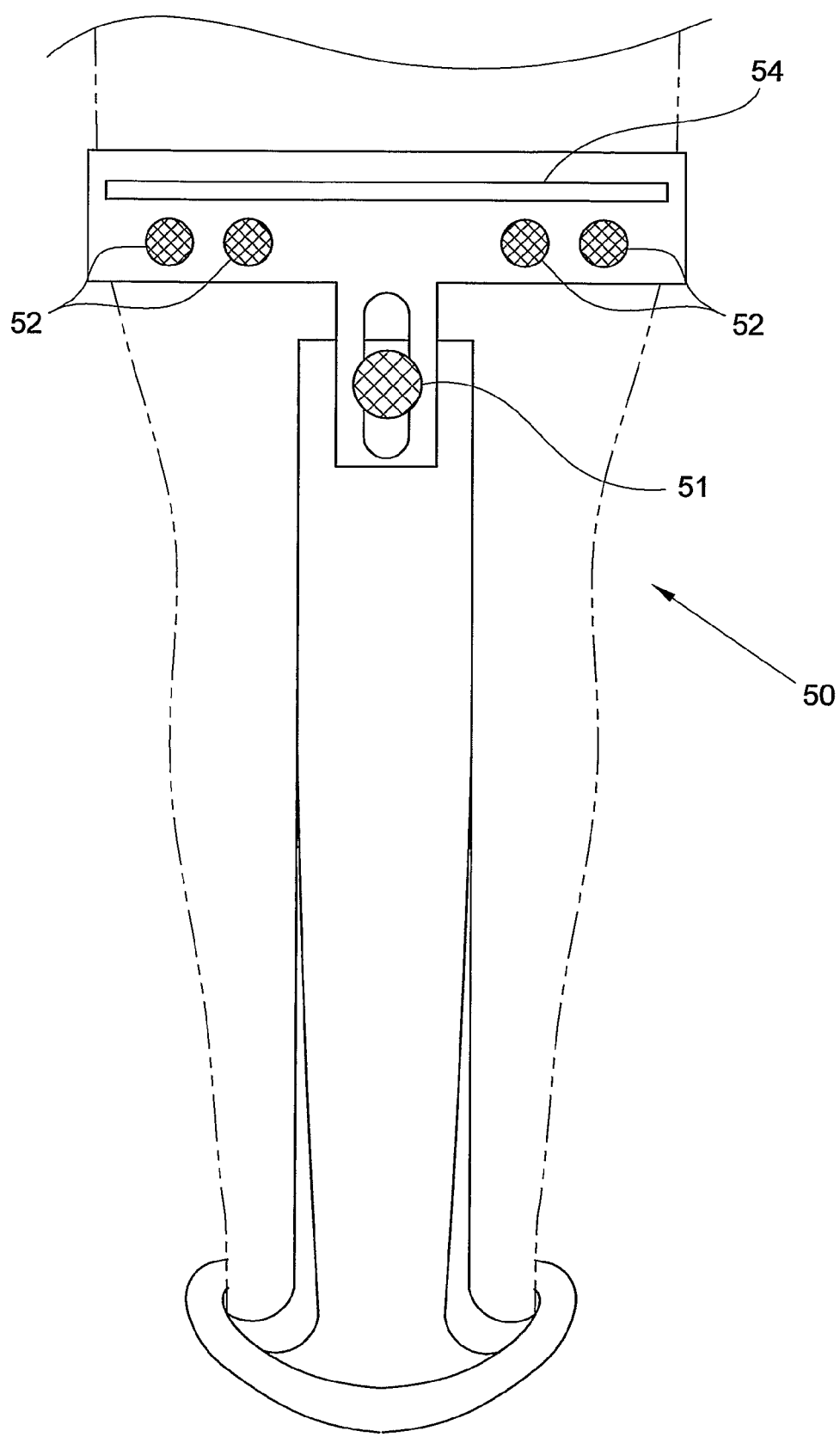
FIGS. 10 and 11 are simplified views of an arrangement for use in marking the location of the proximal tibia and guiding resection thereof.

As depicted in FIGS. 9 and 10, the apparatus 40, in addition to the reflectors 22 comprises a cutting-guide 43 having a slot 44. The cutting guide 43 is mounted to the pin 33 in a manner that allows the orientation of the guide 43 to be suitably adjustable to ensure appropriate positioning of the slot 44 prior to use of a suitable bone resector to form distal cut 13.

Figure 11:
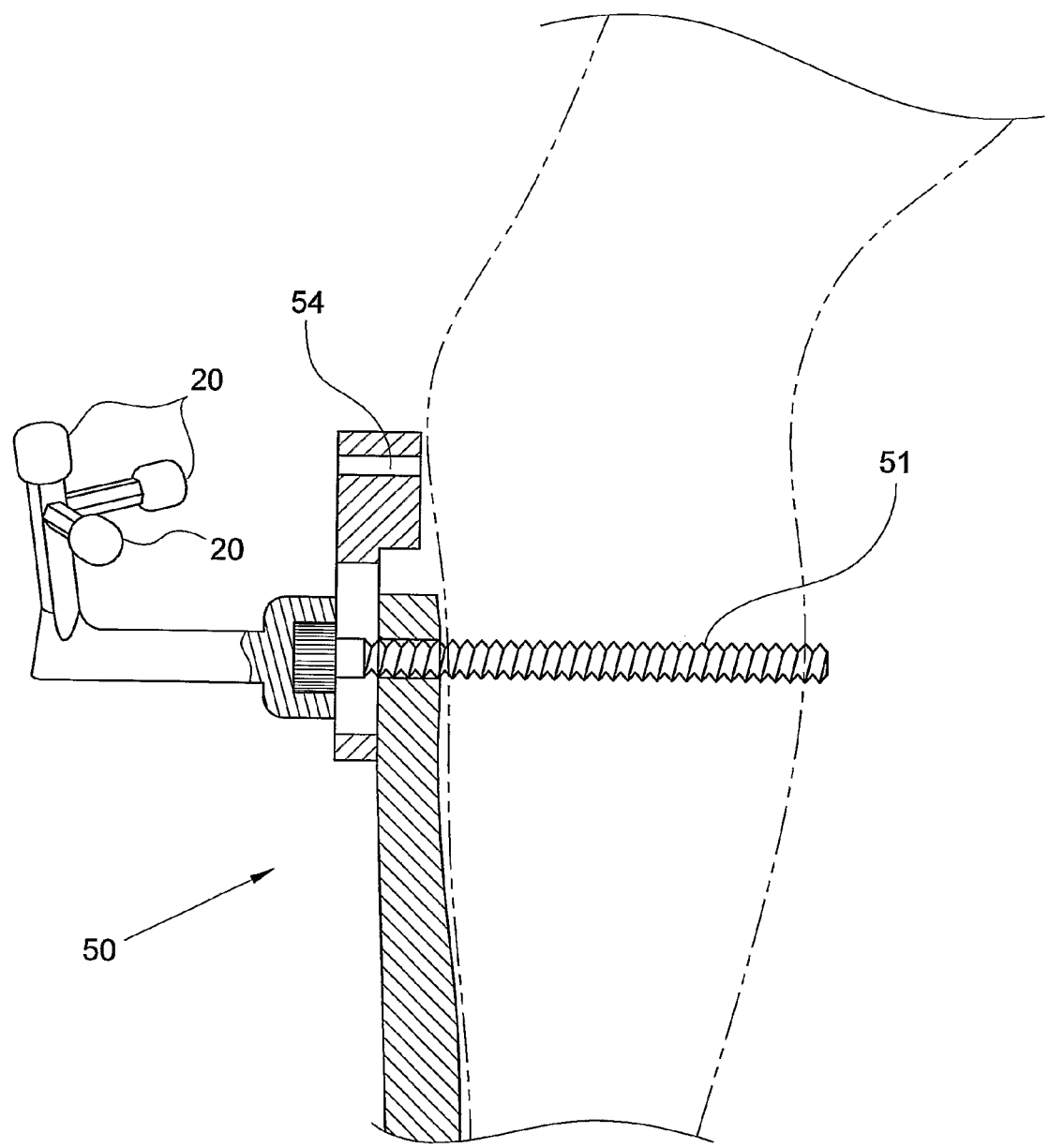

To ensure appropriate mounting of the knee prosthesis, the proximal tibia must also be cut perpendicular to the mechanical axis of the tibia. One embodiment of an apparatus for achieving this is depicted generally as 50 on FIGS. 10 and 11. The device 50 has a distal end that is adjustably mountable to the leg. The length of the apparatus 50 is also adjustable to suit the dimensions of the leg receiving the prosthesis. Fixation of the apparatus 50 is provided by primary and secondary pins 51,52.

A bone marker device, again having a series of reflectors 20, can be mountable to the pin 51. The guiding member has a slot 54 that can be brought into the required position by appropriate adjustment of the apparatus 50. The slot 54, as in the above embodiments, acts as a guide for a bone saw to ensure appropriate resection of the proximal tibia.

Once appropriate bone resection has been made, the femoral and tibial components of the prosthesis can be appropriately positioned and cemented into place with polymethylmethacrylate (PMMA) cement. If an uncemented system is being used, press-fit and bony ingrowth provides the short and long term fixation of the component. At this stage, the tourniquet can be deflated prior to closure to allow accurate haemostasis and the knee joint is usually drained and dressed in extension. The foot pulses are checked at the end of the procedure.

The present invention provides an apparatus that results in navigation markers for use in guided surgery being located at the operative site and even part of the instruments used to appropriately guide the bone saw. The use of such devices allows a modification of the method of performing the necessary resections. Instead of positioning markers, mapping the bone, then placing the instruments to resect the bone, the instruments bearing the bone markers can be positioned, the bone can then be mapped, adjustments to the instruments can be made based on what is found with the mapping and the first appropriate cut can then be made. The remaining cuts can then be made with reference to this first guided cut.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of resecting bone in joint replacement surgery comprising:
removably securing a bone marker device to a bone by connecting the bone marker device to a hole in the bone, wherein the bone has a first portion that is to be removed and a second portion that is not to be removed, and wherein the hole is formed in the first portion of the bone and the hole does not extend to the second portion of the bone;
mapping the bone with the bone marker device;
if required, adjusting the bone marker device;
cutting the bone in accordance with the mapping; and
removing the first portion of the bone including the entire hole.

2. The method of claim 1 comprising removably securing one, two or more than two markers to the bone.

3. The method of claim 2 wherein said markers are reflectors that reflect visible or non-visible light.

4. The method of claim 3 wherein the markers are infra-red markers.

5. The method of claim 2 wherein the markers comprise part of an ultrasonic or electromagnetic system, said system comprising an ultrasonic or electromagnetic emitter or receiver.

6. The method of claim 2 wherein the markers are all of the same type.

7. The method of claim 2 comprising two or more different types of markers.

8. The method of claim 2 wherein the marker is mounted to a post that is connected to a bone pin or bone screw and wherein the step of removably securing the marker comprises inserting the bone pin or bone screw laterally through the hole in the first portion of the bone.

9. The method of claim 8 wherein the post is adjustably or non-adjustably connectable to the bone pin or bone screw.

10. The method of claim 9 wherein the bone pin or bone screw includes a plate member extending outwardly from a portion of the bone pin or bone screw, and wherein the step of removably securing the marker comprises engaging said plate member with an outer surface of the bone.

11. The method of claim 8 wherein the bone screw comprises an elongate body extending from a first end to a second end wherein the entire length of the bone screw is threaded.

12. A method of resecting bone in joint replacement surgery comprising:
connecting a bone pin or bone screw to a location of a bone that is to be removed in joint replacement surgery,
wherein the bone pin or bone screw is adapted so that a bone marker is mounted or mountable to the bone pin or bone screw for use in mapping of the bone,
wherein the bone has a first portion that is to be removed and a second portion that is not to be removed and the bone pin or bone screw is connected only to the first portion; and
wherein the step of connecting the bone pin or bone screw to the first portion of the bone causes damage to the first portion of the bone but not the second portion of the bone; the method further comprising:
mapping the bone with the bone marker;
cutting the bone in accordance with the mapping; and
removing the first portion of the bone including all of the damage caused by the step of connecting the bone pin or bone screw.

13. A method of resecting bone in joint replacement surgery comprising:
connecting a first guide member to an attachment location of a bone that is to be removed in joint replacement surgery,
wherein the bone has a first portion that is to be removed and a second portion that is not to be removed, and wherein the attachment location is on the first portion and the first guide member is connected to the first portion at the attachment location by a bone pin or bone screw that extends into the first portion and not the second portion of the bone;
cutting the bone using, during at least part of the cutting, a bone saw that is guided by the first guide member while the first guide member is connected to the first portion of the bone by the bone pin or bone screw; and removing the first portion of the bone including the attachment location and damage caused by the step of connecting the first guide member to the attachment location.

14. The method of claim 13, wherein the step of cutting comprises making a plurality of cuts in the bone, and wherein the bone saw is guided by the first guide member during a first one of the plurality cuts.

15. The method of claim 14, comprising:
disconnecting the first guide member from the first portion of the bone;
connecting a second guide member to the first portion of the bone; and
making a second cut using a bone saw guided by the second guide member.

16. The method of claim 15, comprising:
disconnecting the second guide member from the first portion of the bone; and
making a third and/or fourth cut using a bone saw, wherein the third and/or fourth cut causes detachment of an area of the first portion of the bone that includes a location position of the bone pin or bone screw that connected the first guide member to the first bone portion.

17. The method of claim 13, wherein the first guide member is pivotally mounted to the bone pin or bone screw.

18. The method of claim 13, wherein the first guide member comprises extender members that are mounted to the pin or bone screw on opposed sides of the bone.

19. The method of claim 18, wherein the first guide member comprises a body member connected between the extender members.

20. The method of claim 19, wherein the body member comprises at least one slot adapted to receive and guide the bone saw.

21. The method of claim 13, wherein the bone to be resected is a femur.

* * * * *